United States Patent [19]

Login et al.

[11] Patent Number: 5,160,729

[45] Date of Patent: Nov. 3, 1992

[54] HIGH WATER CONTENT HAIR SPRAY COMPOSITION

[75] Inventors: Robert Login, Oakland; Carmen D. Bires, Hackettstown; Edward W. Walls, Jr., Cranford, all of N.J.

[73] Assignee: ISP Investments Inc., Wilmington, Del.

[21] Appl. No.: 734,975

[22] Filed: Jul. 24, 1991

[51] Int. Cl.$^5$ .............................. A61K 7/11
[52] U.S. Cl. .......................... 424/47; 424/43; 424/45; 424/70; 424/71; 424/78.02; 424/DIG. 1; 424/DIG. 2; 548/543
[58] Field of Search .......... 424/43, 45, 47, 70, 424/71, 78, DIG. 1, 78.02, DIG. 2; 548/543

[56] References Cited

U.S. PATENT DOCUMENTS

| | | | |
|---|---|---|---|
| 4,543,249 | 9/1985 | Nelson | 424/70 |
| 4,954,335 | 9/1990 | Janchipraponvej | 424/70 |
| 4,954,336 | 9/1990 | Chuang et al. | 424/71 |
| 4,961,921 | 10/1990 | Chuang et al. | 424/47 |

OTHER PUBLICATIONS

CTFA, Helioff et al., 103: 80–84, May 1988 "Alkyl Pyrrolidone Surfactants in Reactive Hair Care Products".

CTFA, Hair Treatment Formulary, 106: 80, 82 Jul. 1991.

Primary Examiner—Thurman K. Page
Assistant Examiner—Robert H. Harrison
Attorney, Agent, or Firm—Walter Katz; Marilyn J. Maue; Joshua J. Ward

[57] ABSTRACT

What is described herein is a high water content hair spray composition which forms uniform, fine spray patterns having rapid drying characteristics and which provides excellent curl retention, and reduced curl droop properties. These results are achieved herein by incorporating a surface active agent or agents into the hair spray composition which agent or agents substantially decreases the surface or interfacial tension of the hydroalcoholic phase of the composition during use. The decreased surface tension of the water-based composition along the length of the hair shaft enhances its spreading tendencies so that substantially no droplets can form upon application of the composition of the hair. The surface active agent preferably is a surface lactive lactam; and, most preferably an N-alkyl pyrrolidone, where the alkyl group is a $C_4$–$C_{22}$, branched or linear, alkyl group.

7 Claims, No Drawings

HIGH WATER CONTENT HAIR SPRAY COMPOSITION

BACKGROUND OF THE INVENTION

1. Field of the Invention

This invention relates to high water content hydroalcoholic hair sprays, and, more particularly, to aqueous and hydroalcohol, non-aerosol and aerosol, hair spray compositions which contain a surface active agent or agents to reduce the surface and interfacial tension of the water or hydroalcoholic phase of the composition thus providing a uniform, fine spray pattern which dries rapidly.

2. Description of the Prior Art

Recent legislation in California and other states has mandated that the amount of volatile organic compounds (VOC) emitted to the atmosphere from commercial hair spray products must not exceed 80% by weight of the composition. In 1998, the VOC level in such products must not exceed 55%. Present hair spray products, however, generally contain large amounts of alcohol above VOC standards. Alcohol functions as a solvent for the resin fixative component of the formulation providing high curl retention, low drying times and low curl droop properties for the user. Accordingly, it is desired to provide hair spray compositions which meet VOC requirements without sacrificing advantageous user properties. The addition of water and removal of alcohol from hair spray compositions will meet VOC requirements; however, such high water content hair sprays lose alcohol as the spray reaches the hair and become more aqueous. As the water level increases so does the surface and interfacial tension. This results in poor wetting and large droplets on the hair. These droplets dry very slowly, particularly as the water content of the composition is increased during dry down, which is objectionable in use because of tack.

Accordingly, it is a particular object of this invention to provide high water content hair spray compositions which satisfy VOC standards and which forms uniform, fine spray patterns which dry rapidly to give effective curl retention, low curl droop, non-tackiness, luster and sheen, low comb drag and a clean feel on the hair without comb residue.

SUMMARY OF THE INVENTION

What is provided herein are aqueous, hydroalcoholic, non-aerosol and aerosol hair spray compositions containing a surface active agent which meet low VOC requirements. Suitably, the hair spray compositions of the invention contain water in the amount of at least 14% by weight, preferably up to 39%, or more; and about 3-10% by weight of a hair fixative resin.

As the feature of the invention, the composition includes an effective amount, generally, 0.1-1% by weight, of a surface active agent or agents which substantially reduces the surface and interfacial tension of the water phase of the composition. Preferably it is an N-alkyl substituted lactam, having from 4-22 carbon atoms, branched or linear, such as N-octyl pyrrolidone.

The hair spray compositions of the invention have significantly more uniform and fine spray patterns, enhanced curl retention, low drying times, and more effective curl droop characteristics than formulations without the added surface active agent. The hair sprays of the invention also are less tacky because they spread out and wet the hair quickly; water can evaporate from this film better; in addition they exhibit less comb drag, have more luster and sheen, and presses a cleaner feel on the hair of the user, than corresponding formulations without the surface active agent.

DETAILED DESCRIPTION OF THE INVENTION

The non-aerosol hair spray compositions of the invention have the following essential and preferred components:

TABLE 1

| | % by Weight | |
|---|---|---|
| | Suitable | Preferred |
| Essential Components | | |
| Resin | 3–10 | 4–6 |
| Water | at least 14 | at least 39 |
| Alcohol | 80 or less | 55 or less |
| Surface Active Agent | 0.1–1 | 0.2–0.4 |
| Preferred Component | | |
| Base | 0.1–0.3 | 0.2 |

The aerosol compositions of the invention have the following constitution:

TABLE 2

| | % by Weight |
|---|---|
| Concentrate (non-aerosol composition) | 50–80 |
| Propellant of Table 1 | 20–50 |

Any suitable hair fixative resin, or mixture of resins, commonly used in hair spray compositions may be used in the formulations of the present invention. Accordingly, the resins described in U.S. Pat. Nos. 4,954,336; 3,927,199; 3,810,977; 3,577,517; 3,405,084; 4,689,379; 4,521,404; 4,315,910; 4,243,548; 4,164,562; 4,897,262; 4,059,688; 4,348,380; 3,862,306; 4,567,035; 4,767,613; 4,543,249; 4,196,190; 4,192,861; 3,981,987; are suitable resin candidates for use herein. The disclosures in these patents are incorporated by reference herein.

The preferred hair fixative resins are alkyl vinyl ether/maleic anhydride half-ester resins (Gantrez ® ES copolymers); or vinyl acetate/monobutyl maleate/isobornyl acrylate resins (Advantage ® CP terpolymers).

Since it is desired to meet current and future VOC requirements for hair spray resin compositions, it is necessary that the compositions herein include at least 14% by weight water, and, preferably, at least 39% by weight water; in such low VOC compositions the alcohol content will comprise only 80% by weight or less, preferably only 55% by weight or less, of the composition.

Usually an organic base, such as amino-methyl propanol, in the amount of about 0.1–0.3% by weight, preferably about 0.2% by weight, is included in the composition to further solubilize the resin component.

The surface active agent used in the hair spray compositions of the invention will substantially decrease the surface or interfacial tension of the water phase of the composition even at water levels reaching an aqueous system. In the preferred form of the invention, the surface tension of the water solution is substantially constant from 14% water to an aqueous composition. During use, the decrease in the surface tension of the solution provides a uniform, fine spray which spreads, evenly along the entire length of the hair shaft. The spreading tendency of the spray on the hair shaft assures that substantially no liquid droplets are formed during use. Furthermore, the thus-applied hair spray, dries very rapidly on the hair of the user which is decidedly advantageous in a water-based product.

A preferred hydroalcoholic, non-aerosol hair spray formulation of the present invention has the following composition.

TABLE 3

| Component | % by Weight |
|---|---|
| Gantrez ® ES-225* or Advantage ® CP** Resin Content | 5.5 |
| Water | 14.0 |
| Ethanol (VDA 40-2/100%) | 80.0 |
| Aminomethyl propanol (AMP) | 0.2 |
| Surfadone ® LP-100*** | 0.3 |
| | 100.0 |

*methyl vinylether-maleic anhydride ethyl half-ester; - GAF Chemicals; 50% active resins in alcohol;
**vinyl acetate-monobutyl maleate-isobornyl acrylate terpolymer ((GAF Chemicals)
***N-octyl pyrrolidone - GAF Chemicals These hair spray compositions were tested for curl retention, drying time and curl droop properties by the standard test procedures manner of the art, and compared with similar formulations without the surface active lactam, and a similar amount of a surfactant. The test results are as follows:

TABLE 4

| Test Sample | Curl Retention (Ave. % Curl after 90 minutes) | Drying Times (Seconds) | Curl Droop Ave. % Droop |
|---|---|---|---|
| 1. Composition of Invention | 70 | 125 | 6 |
| 2. Same Composition without Surface Active Lactam | 55 | 165 | 20 |
| 3. Same Composition with Igepal ® nonylphenoxy ether or Aerosol OT ® (2-ethylhexyl) sulfosuccinate | 55 | 150 | 20 |

The comparative tests given in Table 4 demonstrate that the compositions of the present invention, which contain a surface active lactam, exhibit substantially improved curl retention, lower drying times and more effective curl droop properties, than similar compositions without the surface active lactam, or compositions which include a surfactant which does not substantially reduce the surface tension of the water solution.

Furthermore, these tests were extended to compare other user characteristics; it was found that the compositions of the invention exhibited more uniform, fine spray patterns, less tackiness, less comb drag, more luster and sheen, and a cleaner feel on the hair than similar compositions without the effective surface active agent therein.

Aerosol compositions are prepared from the concentrate of the non-aerosol formulation using any suitable propellant known in the art for use in aerosol hair sprays. Usually about 50-80% by weight of the concentrated (non-aerosol composition), and about 20-50% by weight of the propellant, is used to prepare the aerosol hair spray composition of the invention. Typical and suitable propellants are described in the aforementioned U.S. patents. Among the preferred propellants are hydrocarbons, such as isobutane and propane ethers such as dimethyl ether; compressed gas such as carbon dioxide, $N_2$ and the like; and mixtures thereof. Both single-phase and two-phase aerosol systems may be used, although a single-phase system is preferred.

A preferred aerosol formulation is as follows:

TABLE 5

| Gantrez ® ES-225 or Advantage ® CP | 3.0 |
|---|---|
| Water | 16.5 |
| Ethanol (100%) | 45.0 |
| Surfadone LP-100 | 0.3 |
| AMP | 0.2 |
| Dimethyl ether | 35.0 |
| | 100.0 |

The aerosol formulations perform in use in a similar manner as their non-aerosol counterparts.

Other surface active agents which are known in the art to reduce surface or interfacial tension and which meet the test of wetting out effectively along substantially the entire length of the hair shaft may be used herein.

While the invention has been described with particular reference to certain embodiments thereof, it will be understood that changes and modifications may be made which are within the skill of the art. Accordingly, it is intended to be bound only by the following claims, in which:

What is claimed is:

1. A low VOC hair spray composition which forms uniform, fine liquid spray patterns on hair which are spread out along substantially the entire length of the individual hair shafts so that substantially no liquid droplets remain thereon consisting essentially of about 3-10% by weight of a hair fixative resin, at least 14% by weight of water, 80% by weight or less of an alcohol, and about 0.1-1% by weight of an N-alkyl pyrrolidone having an alkyl group with from 4-22 carbon atoms.

2. A low VOC hair spray composition according to claim 1 wherein said surface active lactam is an N-alkyl pyrrolidone where the alkyl group has from 8 to 12 carbon atoms.

3. A low VOC composition according to claim 2 where said surface active lactam is N-octyl pyrrolidone.

4. A low VOC hair spray composition according to claim 3 wherein said N-octyl pyrrolidone is present in an amount of about 0.2 to 0.4% by weight.

5. A low VOC aerosol hair spray formulation which comprises about 50-80% by weight of the concentrate of claim 1 and about 20-50% by weight of a propellant.

6. A low VOC aerosol hair spray formulation according to claim 5 wherein said propellant is selected from hydrocarbons, ethers and compressed gases.

7. A method of treating hair with a high water content, low VOC hair spray to effect a resin holding action on the individual hair shafts of the user comprising:
(a) applying a uniform, fine liquid spray pattern of the composition of claim 1 to the hair of the user,
(b) spreading out the liquid spray along substantially the entire length of the individual hair shafts so that substantially no liquid droplets remain thereon,
(c) rapidly drying the thus-spread out water-based composition, thereby to effect excellent hair curl retention and low curl droop without hair tackiness, comb drag, and without leaving excessive resin residue on the hair.

* * * * *